(12) United States Patent
Tae et al.

(10) Patent No.: US 8,765,672 B2
(45) Date of Patent: Jul. 1, 2014

(54) METHOD OF MODULATING RELEASE OF BIOMOLECULES HAVING HEPARIN-BINDING AFFINITY

(75) Inventors: Giyoong Tae, Gwangju (KR); Bo-young Kim, Gwangju (KR); Kihak Gwon, Gwanju (KR); Young Ha Kim, Gwangju (KR); Myung-Han Yoon, Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 1 day.

(21) Appl. No.: 13/550,136

(22) Filed: Jul. 16, 2012

(65) Prior Publication Data
US 2013/0112544 A1    May 9, 2013

(30) Foreign Application Priority Data
Nov. 8, 2011    (KR) .................. 10-2011-0115708

(51) Int. Cl.
| | | |
|---|---|---|
| *C07K 14/50* | (2006.01) | |
| *C07K 17/06* | (2006.01) | |
| *C07K 17/14* | (2006.01) | |

(52) U.S. Cl.
USPC ............... 514/9.1; 514/56; 530/350

(58) Field of Classification Search
None
See application file for complete search history.

(56) References Cited

U.S. PATENT DOCUMENTS 6,617,027 B2 *    9/2003    Kim et al. .................. 428/411.1

OTHER PUBLICATIONS

Jensen et al., Loading into and electro-stimulated release of peptides and proteins from chondroitin 4-sulphate hydrogels, Eur. J. of Pharm. Sci. 15(2002)139-148.*
Lee and Shin, Matrices and scaffolds for delivery of bioactive molecules in bone and cartilage tissue engineering, Advanced Drug Delivery Reviews 59 (2007) 339-359.*
On-cue detachment of hydrogels and cells from optically transparent electrodes, Kim et al., Chem. Commun., 2009, 5865-58967.*
Sustained Release of Human Growth Hormone from Heparin-Based Hydrogel, Choi et al., Biomacromolecules 2008, 9, 1698-1704.*

\* cited by examiner

*Primary Examiner* — Maury Audet
*Assistant Examiner* — Joseph Fischer
(74) *Attorney, Agent, or Firm* — Nath, Goldberg & Meyer; Joshua B. Goldberg

(57) ABSTRACT

The present invention relates to a method of modulating a release of biomolecules having heparin-binding affinity, and more specifically, to a method of modulating a release of biomolecules having heparin-binding affinity, using thiolated heparin adsorbed on metal surface. According to the present invention, it is possible to modulate various biomolecules having heparin-binding affinity such as growth factors spatiotemporally by external electrical stimulations, without causing cytotoxicity and having deteriorating effects on cell activity. Thus, the present invention can be applied for various biomedical and biotechnical fields including drug delivery, biosensor, and cell culture.

6 Claims, 15 Drawing Sheets

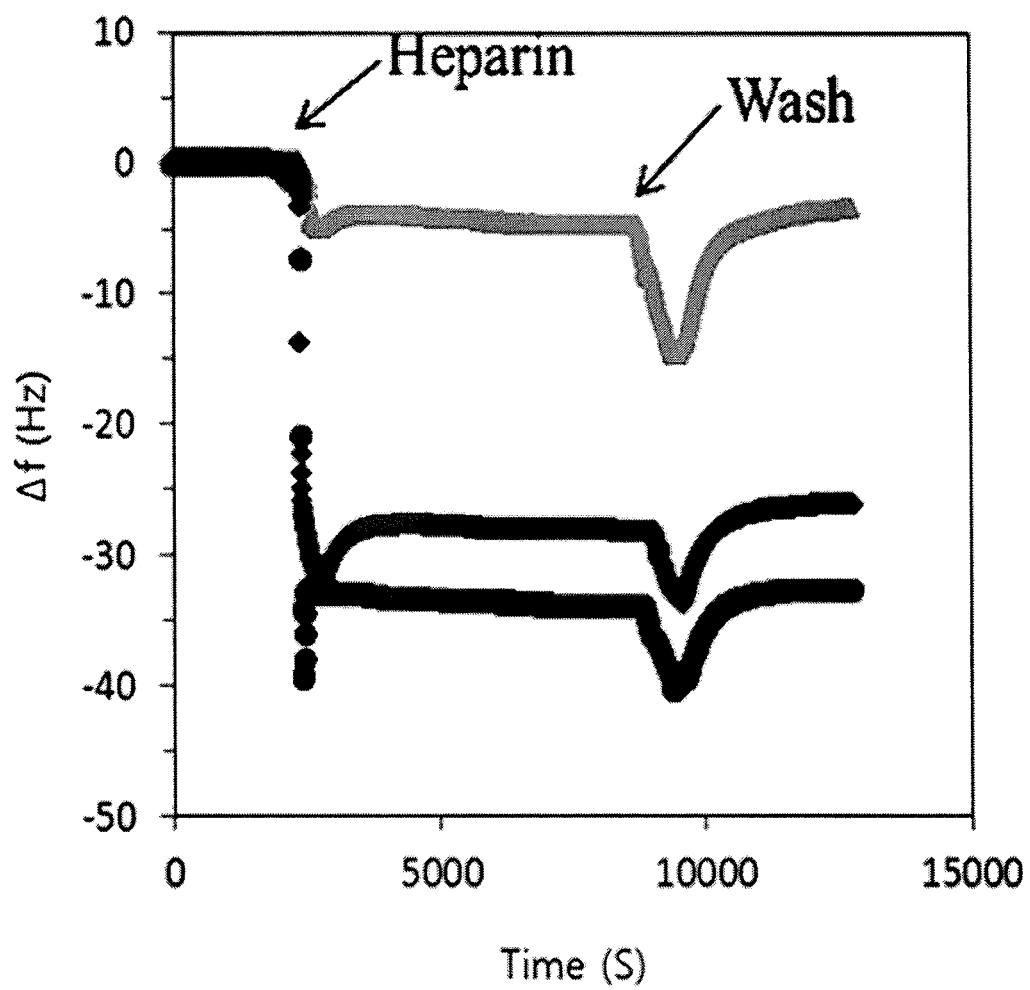

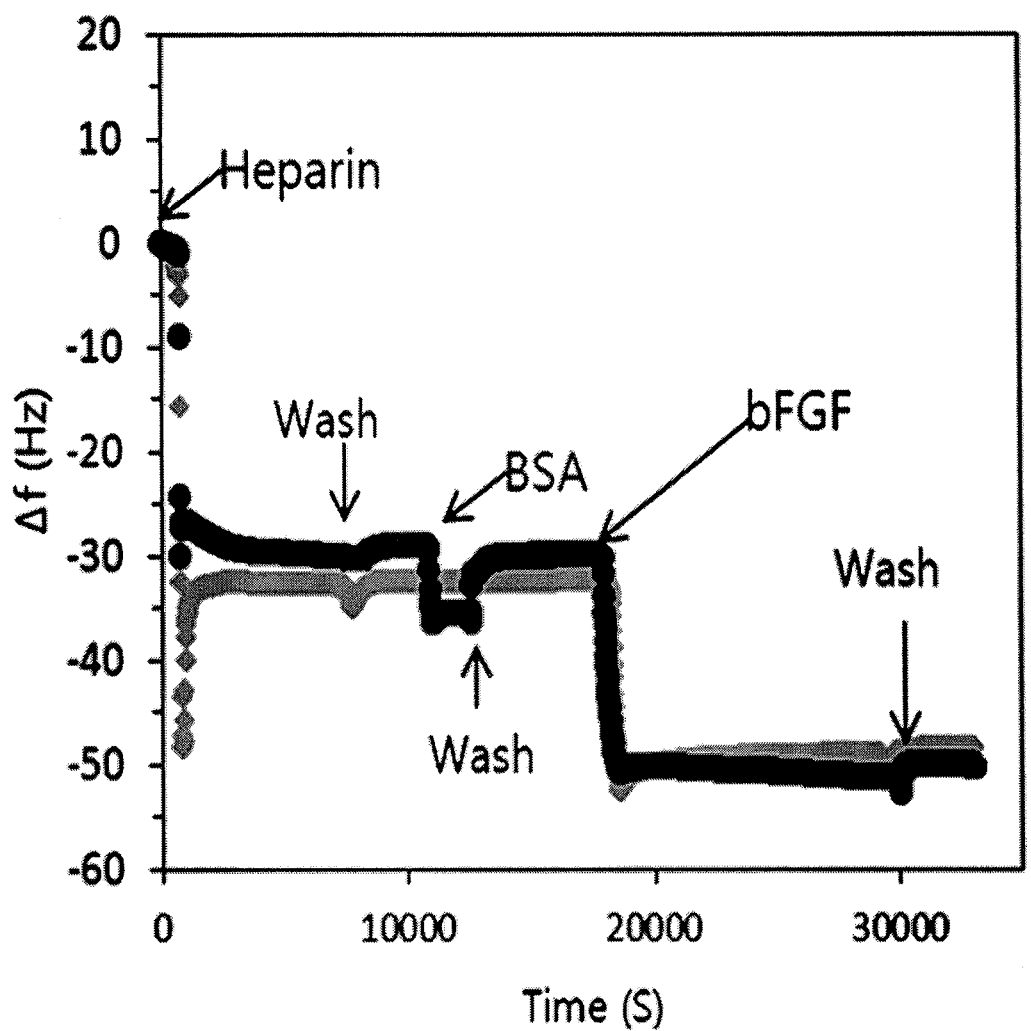

METHOD OF MODULATING RELEASE OF BIOMOLECULES HAVING HEPARIN-BINDING AFFINITY

CROSS-REFERENCE TO RELATED APPLICATION

This application claims priority to Korean Patent Application No. 10-2011-0115708 filed on Nov. 8, 2011, and all the benefits accruing therefrom under 35 U.S.C. §119, the contents of which are incorporated by reference in their entirety.

BACKGROUND

The present invention relates to a method of modulating a release of biomolecules having heparin-binding affinity, and more specifically, to a method of modulating a release of biomolecules having heparin-binding affinity, using thiolated heparin adsorbed on metal surface.

A controlled release in response to external stimuli has been actively studied for the delivery of biomolecules such as proteins, DNA, peptides, and drugs. As external stimuli, pH change, temperature change, magnetic modulation, and electrical stimulation have been applied. Particularly, the advantage of electrical stimulation among external stimulations is that it can be applied locally within a designated region, with a precisely controlled time profile, thus spatiotemporal modulation is possible. In addition, electrical stimulation does not harm biological functions of biomolecules, cells, and organs in some limited ranges, so it is regarded as a relatively biocompatible means for in vivo application.

There have been many reports of electrochemically controlled release of charged molecules such as proteins and drugs based on polymers with two distinctive redox states, where one state is suitable for binding of target molecules and the other state accelerates the release of them. Electrodes serve to switch the redox states and the magnitude of applied current can control the release amount of molecules. For example, neurotrophin-3 (NT-3) and brain-derived neurotrophic factor (BDNF) incorporated into polypyrrole redox layer were released by the control of applied current. NT-3 and BDNF released from the polymer redox layer enhanced the survival of neuron and the elongation of neurites (Burgmayer P, Royce W. M. An ion gate membrane: electrochemical control of ion permeability through a membrane with an embedded electrode, *Journal of the American Chemical Society* 1982, 104, 6139-6140; Thompson. B. C, Richardson, R. T., Moulton, S. E., Evans, A. J, O'Leary, S, Clark, G. M., Wallace, G. G. Conducting polymers, dual neurotrophins and pulsed electrical stimulation-Dramatic effects on neurite outgrowth, *Journal of Controlled Release* 2010, 141, 161-167). Multilayer by layer-by-layer assembly was also employed to contain negatively charged Prussian blue nanoparticles as electroactive component and positively charged drugs via electrostatic interaction. Then, upon the application of electrical stimulation, multilayers were dissolved by a charge shift due to the oxidation of Prussian blue nanoparticles and the incorporated drugs were released accordingly (Daniel J. Schmidt, Joshua S. Moskowitz, Paula T. Hammond. Electrically Triggered Release of a Small Molecule Drug from a Polyelectrolyte Multilayer Coating, *Chemical of Materials*, 2010, 22, 6416-6425). These approaches have an advantage of incorporating a variety of molecules regardless of size, shape or chemical composition.

As an another approach of electrochemically controlled release of molecules, a reaction between gold and sulfur compounds has been used using the strong affinity of sulfur compounds to a transition metal surface. Examples of these surface active sulfur compounds include di-n-alkyl sulfide, thiophenols, mercaptopyridines, alkanethiolates, and cysteines. Among them, thiolates (RS—) have been studied extensively in recent years. They can be chemisorbed on gold surface by the oxidization of S—H group, which makes a quite strong binding (the absorption energy of Au—S bond is ≈44 kcal/mol.) (Dubois, L. H, Nuzzo, R. G. Synthesis, structure, and properties of model organic surfaces, *Annual Review of Physical Chemistry*, 1992, 43, 437-463). Especially, alkanethiols can easily form a uniform self-assembled monolayer (SAM) on gold surface, thus have been applied for molecular detections and recognitions, which can be detected by electrochemical measurement (Orozco, J, Medlin, L. K. Electrochemical performance of a DNA-based sensor device for detecting toxic algae, *Sensors and Actuators B: Chemica* 2011, 153, 71-77; Kim. G. I, Kim. K. W, Oh. M. K, Sung. Y M. Electrochemical detection of vascular endothelial growth factors (VEGFs) using VEGF antibody fragments modified Au NPs/ITO electrode, *Biosensors and bioelectronics* 2010, 25, 1717-1722; Miao. P, Liu. L, Nie. Y, Li. G. An electrochemical sensing strategy for ultrasensitive detection of glutathione by using two gold electrodes and two complementary oligonucleotides, *Biosensors and bioelectronics,* 2009, 24, 3347-3351).

More importantly, chemisorbed thiolates (RS—) can be electrochemically desorbed from gold surface by the reduction of sulfur when negative potentials are applied (Noshir S. Pesika, Kathleen J. Stebe, Peter C. Kinetics of Desorption of Alkanethiolates on Gold, *Langmuir* 2006, 22, 3474-3476; Ulman. A; Formation and Structure of Self-Assembled Monolayers, *Chemical Review,* 1996, 96, 1533-1554).

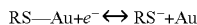

RS—Au+e⁻ ↔ RS⁻+Au

Thus, the electrochemical desorption of thiols has been applied as a means of controlled release of immobilized materials (e.g., biomolecules, channel compounds, DNAs, and subcellular release) by electrical stimulation. However, only burst release of immobilized molecules is possible by this method, and since alkanethiols are not perfectly biocompatible, the remaining alkanethiols along with the released molecules may cause problems in further use.

Heparin, a natural polysaccharide, has been used as an antithrombotic drug, but also has strong binding affinity for a variety of growth factors (e.g., endothelial growth factors (EGFs), fibroblast growth factors (FGFs), and hepatocyte growth factors (HGFs)) via specific heparin-binding domains in these molecules. Based on this specific binding with growth factors, heparin immobilization on various surfaces has been employed for controlled release of growth factors while maintaining their bioactivities (Hong S., Xixue H., Fei Y., Jianzhong B., Shenguo W. Cell affinity for bFGF immobilized heparin-containing poly(lactide-co-glycolide) scaffolds, *Biomaterials,* 2011, 32, 3404-3412; Cionne N. M, H. Mike K, Shelly S. E, Leesa M. G, Necat H, Stavros T. Sustained delivery of transforming growth factor beta three enhances tendon-to-bone healing in a rat model, wiley online library, 2011, 29,1099-1105). A method of releasing growth factors slowly using a heparin-based hydrogel was also disclosed as a conventional art, in which heparin is thiolated by modifying carboxylic acid group of heparin with cysteamine to prepare thiolated heparin, and then the thiolated heparin is cross-linked to form the heparin-based hydrogel (Tae, G, Kim, Y. J, Choi, W. I, Kim, M, Stayton, P. S, Hoffman, A. S. Formation of a novel heparin-based hydrogel in the presence of heparin-binding biomolecules, *Biomacromolecules* 2007, 8, 1979-1986). Here, thiolation of heparin reduces the anticoagulant activity of heparin, but the binding affinity with growth factors is not much affected by the thiolation. Whereas simple immobilization of heparin to surface of gold particles, etc. or the use of the heparin-based hydrogel can allow a temporary release or continuous sustained release of growth factors bound on heparin, these cannot modulate a release rate in accordance with time. Therefore, there are needs for methods for modulating the release rate of growth factors by an external signal, such as electrical stimulation, at a desired time.

SUMMARY

The present disclosure provides a method of modulating a release rate of various biomolecules having heparin-binding affinity such as growth factors by an external signal, the method which does not cause cytotoxicity and have any deteriorating effects on cell activity.

In accordance with an exemplary embodiment of the present invention, a method of modulating a release of biomolecules having heparin-binding affinity includes: preparing thiolated heparin by modifying carboxylic acid group of heparin; chemisorbing the thiolated heparin on metal surface by oxidation; binding biomolecules having heparin-binding affinity to the adsorbed heparin; and causing the release of the biomolecules having heparin-binding affinity by applying electrical stimulation to the complex of metal surface, heparin, and biomolecules having heparin-binding affinity.

In accordance with another exemplary embodiment of the present invention, the thiolated heparin may be prepared by reacting the heparin with cysteamine.

In accordance with another exemplary embodiment of the present invention, the metal may be biocompatible, and able to react with a thiol group.

In accordance with another exemplary embodiment of the present invention, the metal may be one or more metals selected from the group consisting of gold, silver, and platinum.

In accordance with another exemplary embodiment of the present invention, the biomolecules having heparin-binding affinity may be growth factors or proteins, having a heparin-binding domain.

In accordance with another exemplary embodiment of the present invention, the biomolecules having heparin-binding affinity may be one or more substances selected from the group consisting of endothelial growth factors (EGFs), fibroblast growth factors (FGFs), vascular endothelial growth factor (VEGF), and hepatocyte growth factors (HGFs).

In accordance with another exemplary embodiment of the present invention, the electrical stimulation may be an application of current from about 100 μA to about −500 μA or application of potential from about 1.5 V to about −2.0V.

In accordance with another exemplary embodiment of the present invention, the electrical stimulation may be an application of current from about 20 to about −100 μA.

BRIEF DESCRIPTION OF THE DRAWINGS

Exemplary embodiments can be understood in more detail from the following description taken in conjunction with the accompanying drawings, in which:

FIG. 3a is a diagram showing frequency change (Δf) and FIG. 3b is a diagram showing dissipation change (ΔD), observed during the chemisorptions of heparin, Hep-SH with 10% thiolation, and Hep-SH with 40% thiolation in QCM-D analysis.

FIG. 5a is a diagram showing frequency change (Δf) and FIG. 5b is a diagram showing dissipation change (ΔD), observed by the sequential addition of Hep-SH (40% thiolation) and bFGF on gold or by the sequential addition of Hep-SH (40% thiolation), BSA, and bFGF on gold in QCM-D analysis.

FIGS. 9a, 9c, and 9e) or potential stimulation (0.2/−0.8 V; FIGS. 9b, 9d, and 9f) was applied as electrical stimulations.

DETAILED DESCRIPTION OF EMBODIMENTS

A method of modulating a release of biomolecules having heparin-binding affinity of the present invention includes: preparing thiolated heparin by modifying carboxylic acid group of heparin; chemisorbing the thiolated heparin on metal surface by oxidation; binding biomolecules having heparin-binding affinity to the adsorbed heparin; and causing the release of the biomolecules having heparin-binding affinity by applying electrical stimulation to the complex of metal surface, heparin, and biomolecules having heparin-binding affinity.

Figure 1:
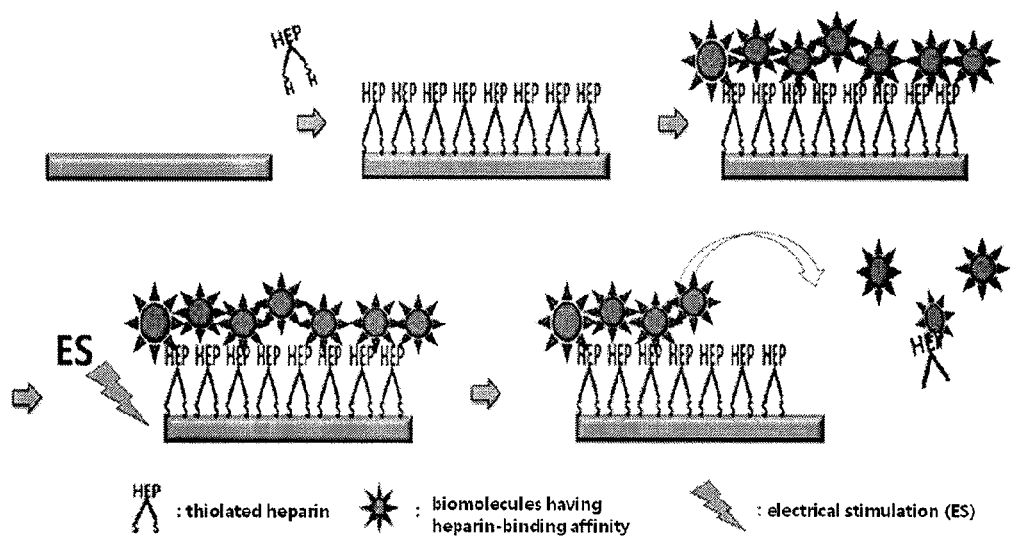
FIG. 1 is a schematic diagram of a method according to the present invention.

Hereinafter, the present invention will be described in more detail with reference to the accompanying drawings. FIG. 1 shows a schematic diagram of the method of modulating a release of biomolecules having heparin-binding affinity according to the present invention. By reference to FIG. 1, first, thiolated heparin having various degree of thiolation may be prepared by modifying carboxyl group of heparin to thiol group. Preferably, the modification of carboxyl group of heparin to thiol group may be carried out by reacting heparin with excess amount of cysteamine.

Next, chemisorbing the thiolated heparin on metal surface is carried out. Herein, any metal which is biocompatible and able to react with a thiol group may be used for the metal, and examples of the metal may include, but not limited to, one or more selected from the group consisting of gold, silver, and platinum.

Next, binding biomolecules having heparin-binding affinity to heparin adsorbed on the metal surface is carried out. General biomolecules having heparin-binding affinity may be used without special limitation for the biomolecule having heparin-binding affinity. For example, the biomolecules having heparin-binding affinity may be growth factors or proteins, having a heparin-binding domain. Specific examples of the growth factors or proteins, having a heparin-binding domain, may include, but not limited to, one or more selected from the group consisting of endothelial growth factors (EGFs), fibroblast growth factors (FGFs), vascular endothelial growth factor (VEGF), and hepatocyte growth factors (HGFs).

Lastly, in the present invention, the release of the biomolecules having heparin-binding affinity is facilitated by applying a suitable electrical stimulation to the complex of metal surface, heparin, and biomolecules having heparin-binding affinity. This can be applied for both in vitro and in vivo systems, and the combination of this system with lithographic technology can control the environment, to which electrical stimulations are applied, using fine lines on a metal membrane, so that this system can be used for the spatiotemporal modulation of the release rate of biomolecules. As described in more detail in the following embodiments, application of a suitable electrical stimulation to the metal surface-heparin-biomolecules having heparin-binding affinity complex leads to a desorption and release of the biomolecules having heparin-binding affinity from the complex, and the release time and rate can be controlled in proportion to the magnitude of applied electrical stimulation. The electrical stimulation may be potential control or current control, and preferably, an application of current from about 100 µA to about −500 µA or application of potential from about 1.5 V to about −2.0V, and more preferably, an application of current from about 20 µA to about −100 µA. Where the applied electrical stimulation is too weak, it is not possible to separate the binding between heparin and biomolecules having heparin-binding affinity, and on the contrary, where the applied electrical stimulation is too strong, the separation of the heparin-biomolecules having heparin-binding affinity complex itself from the metal surface rather than the separation of the binding between heparin and biomolecules having heparin-binding affinity could be occurred, and the biomolecules having heparin-binding affinity could be released in bursts, so, it is difficult to modulate the rate of continuous release. Also, as described in more detail in the following embodiments, where the electrical stimulation to be applied is a current (from about 20 µA to about −100 µA) rather than a potential (from about 1.5 V to about −2.0 V), controlled release of the biomolecules having heparin-binding affinity was easier.

Hereinafter, the present invention will be described in more detail with reference to specific embodiments. However, the following embodiments are described for illustrative purposes only, and do not limit the scope of the present invention.

PREPARATION EXAMPLES

Apparatus and Reagents

Heparin (sodium salt, from porcine intestinal mucosa, MW 1.2 kDa) was purchased from Cellsus, Inc. (Cincinnati, Ohio, USA). 1-Ethyl-3-[3-dimethylaminopropyl]-N'-ethylcarbodiimide hydrochloride (EDC), DL-Dithiotreitol (DTT), and N-ethylmaleimide, Potassium ferricyanide(III) were purchased from Sigma (St. Louis, Mo., USA). 1-hydroxy-benzotriazole (HOBt) hydrate, cysteamine hydrochloride was obtained from Fluka (Buchs, Switzerland). As an Ellman's reagent, 5,5'-Dithiobis(2-nitrobenzoic acid) (DTNB) was purchased from Pierce (Rockford, Ill., USA). Gold coated slides, 1000 Å evaporated with a 50 Å Ti adhesion layer, were purchased from EMF (Ithacha, N.Y., USA). Recombinant human fibroblast growth factor basic (bFGF) was obtained from CHABIO & DIOSTECH Co. (Seoul, Korea). Human FGF-basic ELISA Development Kit was purchased from Peprotech (Rocky Hill, N.J., USA).

Medium Dulbecco's modified Eagles medium (DMEM) with D-glucose and glutamine, Fetal bovine serum (10%), and antibiotics (1%) were purchased from Gibco (Grand island, N.Y., USA). UltraMEM, a culture medium was obtained from LONZA Walkersville Inc. (Walkersville, Md., USA). Balb/c3T3 fibroblast was purchased from Korean Cell Line Bank (Seoul, Korea). Acridine orange (AO) and propidium iodide (PI) were purchased from Sigma Chemical (St. Louis, Mo., USA). WST-8 was purchased from Roche Ltd. (Basel, Switzerland). Dialysis membrane (3.5 kDa Mw cut-off) was purchased from Spectrum lab (Rancho Dominguez, Calif., USA).

Preparation Example 1

Thiolation of Heparin

Carboxyl groups of heparin were converted to thiol groups, following the conventional document (Tae, G, Kim, Y. J, Choi, W. I, Kim, M, Stayton, P. S, Hoffman, A. S. Formation of a novel heparin-based hydrogel in the presence of heparin-binding biomolecules, *Biomacromolecules*, 2007, 8, 1979-1986). Briefly, thiolated heparin (Hep-SH) with various degrees of thiolation was prepared by reacting carboxyl group of heparin with cysteamine. Heparin was dissolved in de-ionized water (DIW) at 10 mg/ml. To this solution, EDC, HOBt, and the excess amount of cysteamine were added sequentially. After reaction for 12 h at room temperature, the solution was thoroughly dialyzed by using a dialysis membrane (3.5 kDa Mw cut-off) to remove unreacted reagents. Then, the excess amount of DTT was added to reduce the oxidized disulfide groups and to form free thiol groups of modified heparin. The degree of thiolation was controllable by adjusting the molar ratios of EDC and HOBt over carboxyl group of heparin. The conversion of carboxylic groups to thiol groups was measured by using an Ellman's reagent at 412 nm.

Preparation Example 2

Preparation of Gold Surface-Heparin-Basic Fibroblast Growth Factor Complex

A gold surface cut into 1.25 $cm^2$ was cleaned by piranha solution (3:1 $H_2SO_4$:$H_2O_2$) for 15 min, followed by sequential rinsing in de-ionized water, and finally dried under nitrogen. In order to make the chemisorbed layer of Hep-SH on the gold surface, the clean gold was immersed into the solution of Hep-SH (1 mg/ml) dissolved in phosphate buffered saline (PBS, pH 7.4) for 90 min at 37° C., followed by a PBS rinse to remove the unreacted Hep-SH. Hep-SH chemisorbed gold surface was subsequently immersed in PBS containing bFGF (2 µg/200 µL) for 3 hours at 37° C. After incubation, the unbound bFGF was removed by washing with PBS for 3 times. The amount of bFGF in washed solution was measured to calculate the bound amount of bFGF on the gold surface.

Example 1

Characterization of Modified Gold Surface by QCM-D

QCM-D (Quartz crystal microbalance with dissipation, E4, Q-sense, Västra Frölunda, Sweden) with Q-Tools software was used to analyze the adsorption of Hep-SH and bFGF on gold surface. QCM-D instrument allows time-resolved and simultaneous analyses of resonance frequency shifts ($\Delta f$) and dissipation change ($\Delta D$) on shear oscillating quartz crystal surface covered with gold electrodes (Q-sense QSX 301, 5 MHz). The frequency shift and the dissipation change were acquired at its first six overtones (i=1, 3, . . . , 11).

The gold-coated QCM crystals were precleaned in 5/1/1 volume ratio of water/ammoniac solution (25%)/hydroxyperoxide (30%) solution for 5 min at 75° C. The clean QCM crystals were installed into the QCM-D chamber, and temperature was set to 37° C. PBS was injected into the chamber and waited until stabilization. Then, Hep-SH (1 mg/mL) dissolved in PBS was injected into the chamber and incubated for 90 min to form chemisorbed heparin layer on gold surface, followed by PBS washing to remove the unbound Hep-SH. Finally, bFGF (2 µg/200 µL) was injected into the chamber to induce the loading of bFGF on heparin and incubated for 3 hours, followed by rinsing with PBS to remove the unbound Hep-SH. To confirm the specific binding of bFGF on heparin, not non-specific binding to gold surface uncovered with heparin, a separate experiment was done with the injection of 1% BSA solution between Hep-SH injection and bFGF injection. All measurements were repeated more than 3 times.

The adsorbed amount ($\Delta m$) can be calculated from the resonance frequency shift ($\Delta f$) based on the well-known Sauerbrey equation (Formula 1).

$$\Delta m = -C \times \Delta f_n / n \qquad \text{<Formula 1>}$$

where C is the mass sensitivity constant (C=17.7 ng·Hz$^{-1}$·cm$^{-2}$ for 5 MHz quartz crystals), and n is the overtone number. In the case of adsorption of soft layer, dissipation factor changed by the adsorbed layer is not negligible. Therefore, the obtained dissipation factor can be used to understand the viscoelastic properties of adsorbed layer.

Example 2

Electrochemical Analysis

All electrochemical measurements were performed with CH Instrument (Austin, Tex., USA) with the conventional three-electrode system consisting of modified gold surface (working electrode), a platinum counter electrode, and an Ag/AgCl reference electrode. The cyclic voltammetry was employed to analyze electrical properties of modified gold surface in PBS (buffer volume: 400 µL, scan rate: 100 mV/sec, scan range: −1 V to 1 V, sensitivity: 1×10$^4$ A/V). In order to optimize the release of bFGF by electrical stimulation, various types of electrical stimulations were applied; monophasic potential (−0.8 V), biphasic balanced potential (±0.2 V), biphasic imbalanced potential (0.2/−0.8V, 0.2/−1.2 V), biphasic balanced current (±20 µA), and biphasic imbalanced current (20/−50 µA, 20/−100 µA, 20/−160 µA, 20/−300 µA). Profiles of electrical stimulations (FIG. 2a) and total amount of released bFGF by each electrical stimulation for 3 hr (FIG. 2b) were shown in FIG. 2a and FIG. 2b, respectively.

Duration of each phase was 1 sec except in case of monophasic potential. The gold surface (electrode) modified with bFGF and heparin was immersed in the release buffer, PBS with 1.1% albumin. Then, different electrical stimulation profile was continuously applied to the gold electrode during the release experiments. After stimulation, buffer solution of 400 µL containing released bFGF were collected and the amount was analyzed by ELISA (n=3).

Example 3

Cytotoxicity of Electrical Stimulation

Cytotoxicity of electrical stimulation used for bFGF release was characterized using Balb/c3T3 clone A31 cells. Cells were seeded on glass (3.0×10$^4$ cells/1.5 cm$^2$ glass) in Dulbecco's modified Eagles medium (DMEM) supplemented with 10% fetal bovine serum (FBS) and 1% antibiotics (Abs) at 37° C./5% $CO_2$. After incubation for 12 hrs, a cells-seeded glass was transferred to an electrode cell containing culture medium of 6 mL. Then, cells were indirectly stimulated with electrical simulation (20/−100 µA) for 1 hr. Live/Dead assay was followed by adding slowly 1 mL of PBS containing 0.67 µM AO and 75 µM PI for 15 min.

Example 4

Bioactivity of bFGF Released by Electrical Stimulation

In order to characterize bioactivity of bFGF released by electrical stimulation, first, bFGF-bound Hep-SH chemisorbed on gold was incubated in the release buffer for 3 days, followed by rinsing with PBS. Then, electrical stimulation was applied for 1 hr and the bioactivity of released bFGF was assayed by using bFGF-dependent proliferation of cells.

Balb/c3T3 clone A31 cells (1.0×10$^4$ cells per well) were cultured in DMEM with 10% FBS and 1% Abs at 37° C./5% $CO_2$. After 8 h of incubation, cells were washed with PBS and then ultra MEM (with 1% Abs) containing either the released bFGF (10 ng/mL) or pristine bFGF (10 ng/mL) was added to each well. Cells were incubated for 2 days, and then cell proliferation was measured by WST-8 assay. After adding the WST-8 reagent to each well, followed by incubation at 37° C. for 90 min, the adsorbance of produced formazan was measured by using a microplate reader at 450 nm. All experiments were performed with n=5.

Evaluation Example 1

Characterization of Chemisorbed Hep-SH on Gold Surface

Figure 3B:
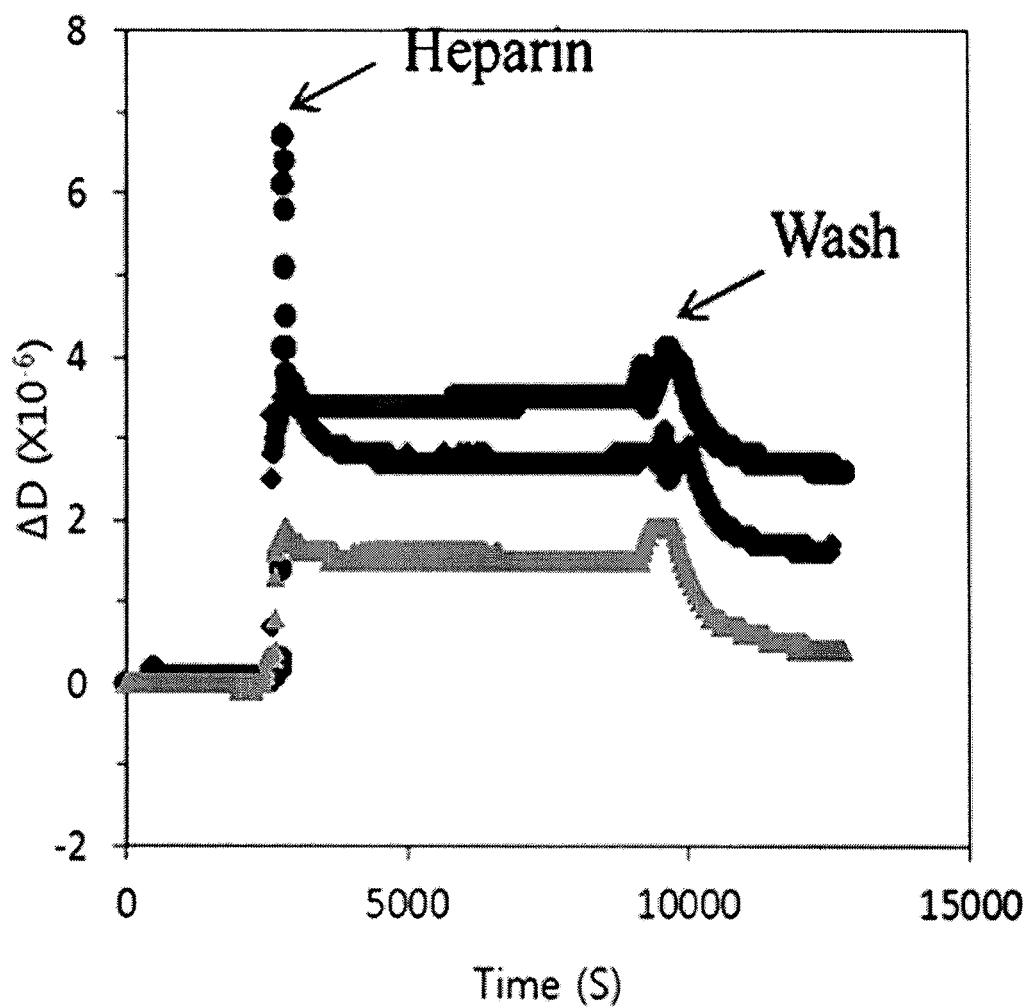

Chemisorption of Hep-SH (10 or 40% thiolation, 1 mg/mL) on gold surface was analyzed by QCM-D. FIG. 3a and FIG. 3b are diagrams showing the changes in frequency ($\Delta f$) (FIG. 3a) and dissipation ($\Delta D$) (FIG. 3b) observed during the chemisorptions of heparin, Hep-SH with 10% thiolation, and Hep-SH with 40% thiolation in QCM-D analysis. Amounts adsorbed on gold were shown with respect to heparin, Hep-SH with 10% thiolation, and Hep-SH with 40% thiolation, respectively, in the following Table 1.

TABLE 1

|  | 40% Hep-SH | 10% Hep-SH | Pure Heparin |
|---|---|---|---|
| Absorbed Hep-SH (ng/cm$^2$) | 550 ± 20 | 430 ± 70 | 60 ± 10 |

By reference to FIG. 3a and FIG. 3b, most changes were achieved within 5-10 min after injecting Hep-SH solution, which means that the chemisorption of Hep-SH on gold surface occurred fast. Larger frequency shift, thus larger amount of chemisorption of Hep-SH on gold surface was observed from Hep-SH with higher degree of thiolation whereas little physical adsorption of pure heparin was observed on gold surface. About 30% of more Hep-SH was adsorbed on gold surface by Hep-SH with 40% thiolation than 10% thiolation (Table 1). Also, the chemisorbed amount remained same after washing, showing the stable adsorption of Hep-SH on gold surface.

Figure 4A:
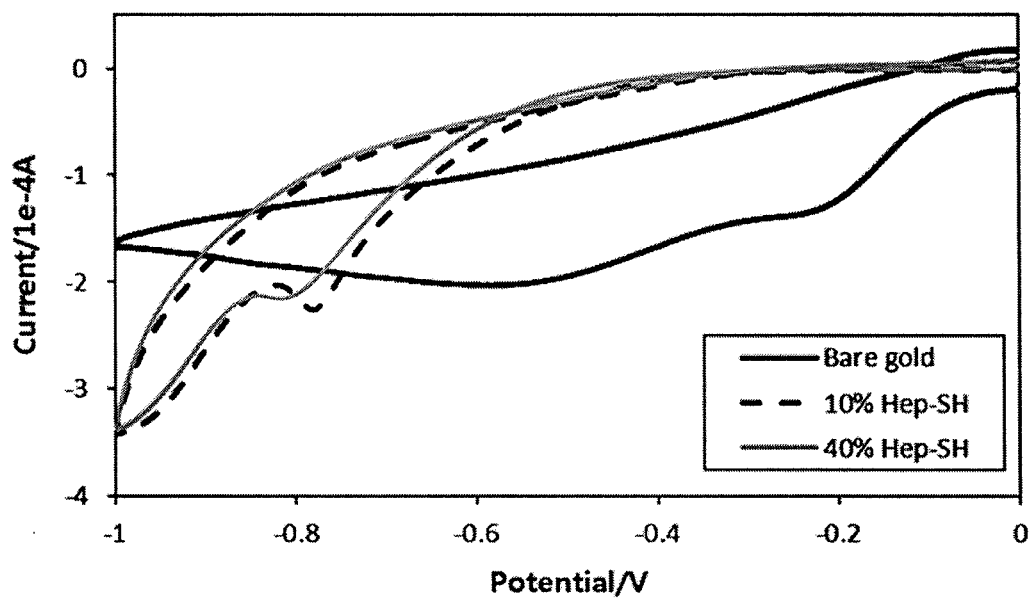
FIG. 4a and FIG. 4b are graphs showing the cyclic voltammogram (CV) curves for bare gold electrode, gold modified with Hep-SH (10% thiolation), and gold modified with Hep-SH (40% thiolation) with respect to different concentrations of Hep-SH (4a: 1 mg/mL; 4b: 0.01 mg/mL).
Figure 4B:
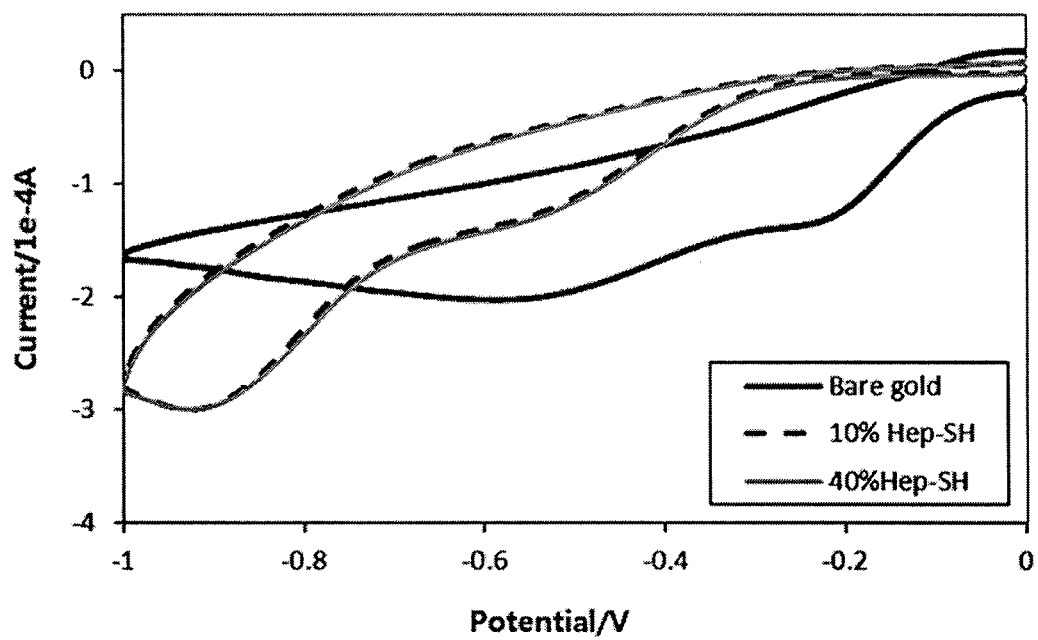

The Hep-SH chemisorbed on gold surface was analyzed by using cyclic voltammetry to confirm the chemisorption and the reductive desorption of Hep-SH. The cyclic voltammogram (CV) curves for bare gold electrode, gold modified with Hep-SH (10% thiolation), and gold modified with Hep-SH (40% thiolation) are shown in FIG. 4a (1 mg/mL of Hep-SH) and FIG. 4b (0.01 mg/mL of Hep-SH). Changes in CV curves compared to bare gold indicate the adsorption of Hep-SH, and the occurrence of electroreductive peaks suggest the occurrence of chemisorption and reductive desorption of Hep-SH on gold.

After chemisorption at 1 mg/mL, the active electrochemical reaction was observed between −0.8 V and −1.0 V at both Hep-SH (10% thiolation) and Hep-SH (40% thiolation). In the case of chemisorption at 0.01 mg/mL, desorption seemed to start at lower reductive potential and clear desorption peak was not observed, probably due to the low density of adsorbed heparin.

Evaluation Example 2

Figure 5B:
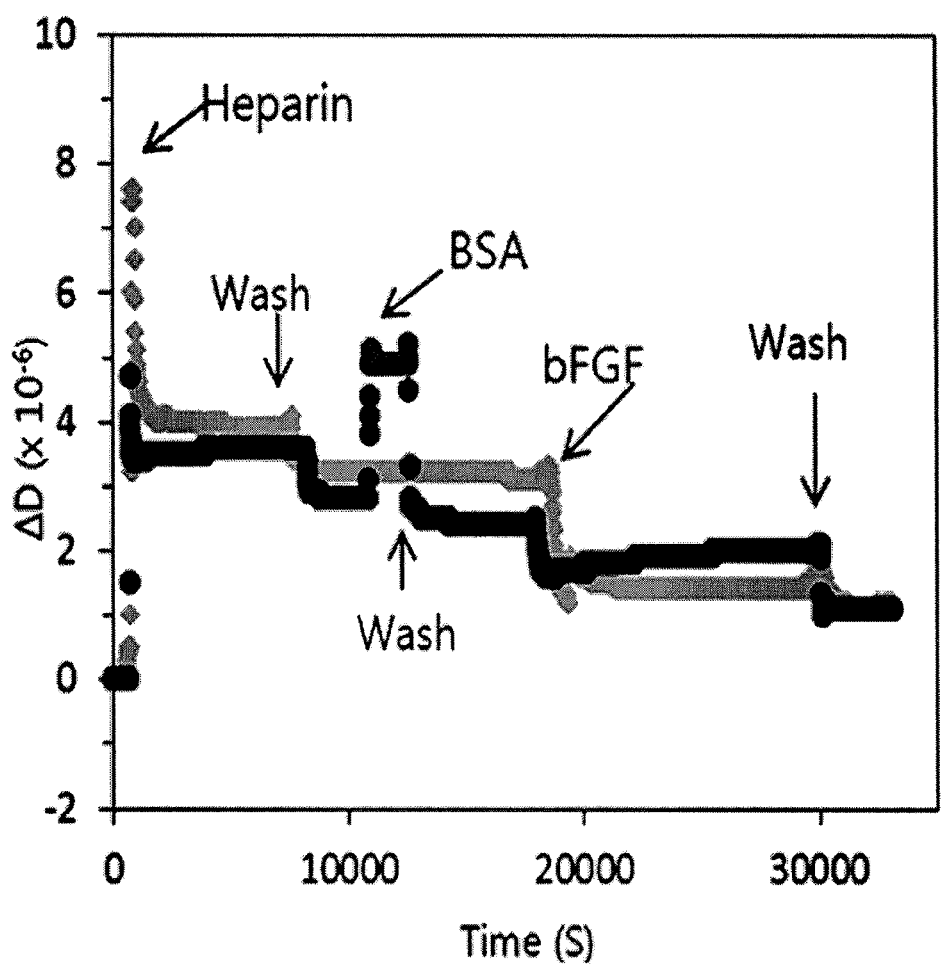

Characterization of bFGF Loaded onto Hep-SH Chemisorbed Gold bFGF loading onto Hep-SH (40% thiolation) adsorbed gold was characterized by QCM-D. FIG. 5a and FIG. 5b are diagrams showing changes in frequency (Δf) (FIG. 5a) and dissipation (ΔD) (FIG. 5b), observed by the sequential addition of Hep-SH (40% thiolation) and bFGF on gold or by the sequential addition of Hep-SH (40% thiolation), BSA, and bFGF on gold in QCM-D analysis. The amount of adsorbed Hep-S-gold and the amount of bFGF adsorbed on Hep-S-gold were shown with respect to Hep-SH with 10% thiolation, Hep-SH with 40% thiolation, and bare gold, respectively, in the following Table 2.

TABLE 2

|  | 10% Hep-SH | 40% Hep-SH | Bare gold |
|---|---|---|---|
| Absorbed Hep-S•gold (ng/cm$^2$) | 430 ± 70 | 550 ± 20 | — |
| Absorbed bFGF on Hep-S•gold (ng/cm$^2$) | 200 ± 70 | 340 ± 30 | 210 ± 30 |

The amount of bFGF bound on immobilized Hep-SH (40% thiolation) was about 70% larger than that of Hep-SH (10% thiolation).

Meanwhile, a considerable amount of bFGF was bound on bare gold. To confirm the specific binding of bFGF via heparin immobilized on gold, 1% BSA solution was injected between Hep-SH and bFGF injection. 1% BSA was temporally bound on Hep-SH chemisorbed gold surface. However, after washing with PBS, BSA was almost completely removed. Also, the adsorbed amount of bFGF was same regardless of bFGF injection and washing. Therefore, these results confirmed that the adsorption of bFGF occurred specifically via heparin immobilized on gold surface, and the chemisorption of Hep-SH on gold was enough to cover the whole surface of gold not to permit non-specific adsorption of bFGF on gold.

Figure 6:
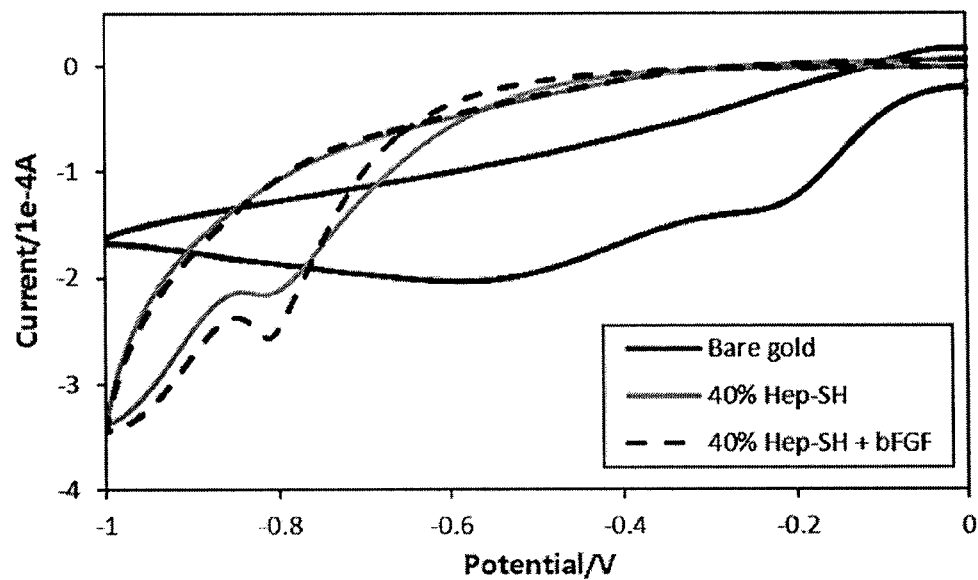
FIG. 6 is a graph showing CV curves of Hep-SH (40% thiolation) chemisorbed gold surface after bFGF loading.

FIG. 6 shows CV curves of Hep-SH (40% thiolation) chemisorbed gold surface after bFGF loading. By reference to FIG. 6, although bFGF was bound on Hep-SH, CV curve was similar to that before bFGF loading, indicating that the adsorption of bFGF on Hep-SH did not cause the change in electrochemical properties of heparin-chemisorbed gold. Based on the peak (~−0.8 V) in CV curves, it could be assumed that a difference in the release behavior of loaded bFGF might occur below and above −0.8 V of applied potential on gold.

A water contact angle measurement was also performed to characterize the change in surface properties of gold surface caused by adsorption of Hep-SH and bFGF, subsequently. Water contact angles measured with a microscope for bare gold (a), Hep-SH (40% thiolation) modified gold (b), and Hep-SH (40% thiolation)/bFGF modified gold (c), respectively are shown in the following Table 3.

TABLE 3

| Experimental process | Contact angle(°) |
|---|---|
| (a) Bare gold | 80 ± 1 |
| (b) 40% Hep(-SH) modified gold | 26 ± 2 |
| (c) 40% Hep(-SH) and bFGF modified gold | 50 ± 2 |

As shown in the above Table 3, the contact angle after chemisorption of hydrophilic Hep-SH (40% thiolation) was decreased to ~26°. In contrast, the contact angle was increased back to ~50° after binding bFGF, because bFGF is relatively hydrophobic compared to heparin due to the possession of several hydrophobic residues such as Tyr24, Tyr103, Leu140, Met142, Phe30, and Leu138.

In summary, it was clearly proved that Hep-SH was chemisorbed to form stable binding on gold by the oxidation of thiol groups, and then bFGF loading was achieved by specific heparin affinity via chemisorbed heparin on gold.

Evaluation Example 3

Modulation of Release Profiles of bFGF by Electrical Stimulation

Figure 2A:
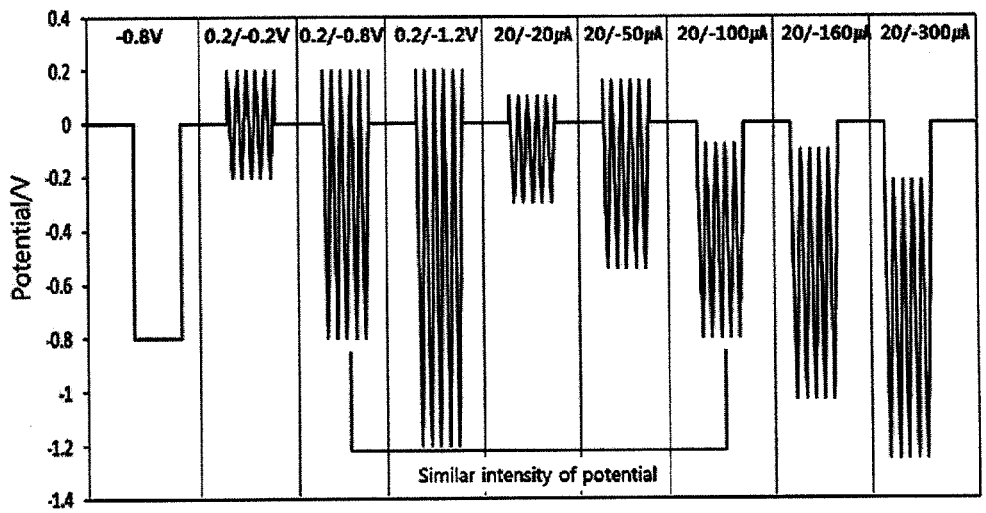
FIG. 2a is a graph showing profiles of electrical stimulations upon application of various types of electrical stimulations.
Figure 2B:
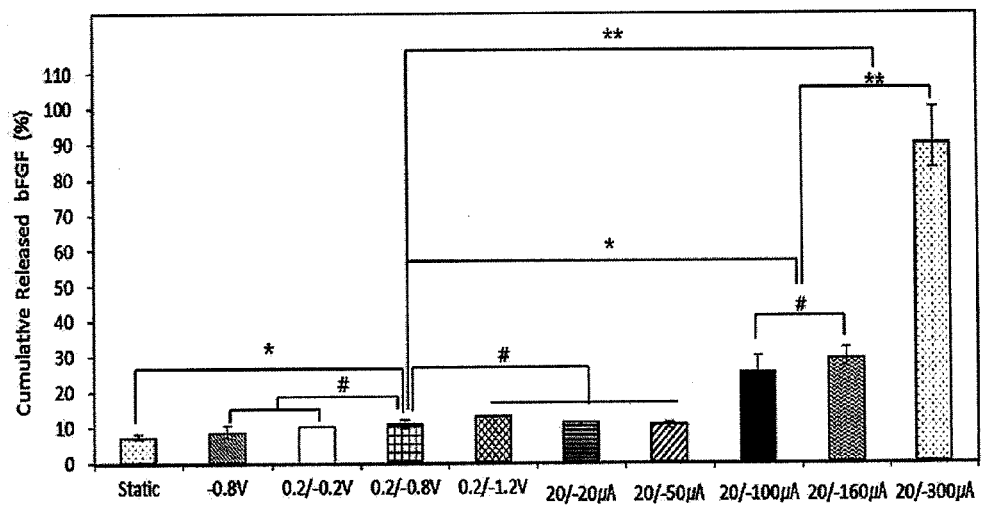
FIG. 2b is a graph showing total amount of bFGF released by each electrical stimulation for 3 hrs.

Release of bFGF loaded on gold electrode modified with Hep-SH (40% thiolation) was measured under various electrical stimulations (FIG. 2a). FIG. 2b shows the release amounts of bFGF by various stimulations for 3 h.

There was no significant difference in the released amount of bFGF either by potential control with −0.8 V, 0.2/−0.2 V or current control with 20/−20 μA, 20/−50 μA (#p>0.05) compared to the control case without electrical stimulation, but statistically significant differences were found by other electrical stimulations compared to the control case (*p<0.05). Also, comparing to potential control of 0.2/−0.8 V, there was no significant difference in the released amount of bFGF by all kinds of potential control and current control with 20/−20

μA and 20/−50 μA. However, the released amount of bFGF was increased significantly by controlling applied current with 20/−100 μA, 20/−160 μA (*p<0.05), or 20/−300 μA (**p<0.001), in proportion to the magnitude of negative current in biphasic application.

Interestingly, comparing the stimulation of 0.2/−0.8 V and 20/−100 μA, both cases showed the similar negative maximum value of generated potential, ~−0.8 V, but the potential control did not provide the stimulated release of bFGF whereas the significantly increased bFGF was observed in the case of the current control. Therefore, the result showed that current control is more effective than potential control to increase the released bFGF from heparin-immobilized gold by electrical stimulation.

Figure 7:
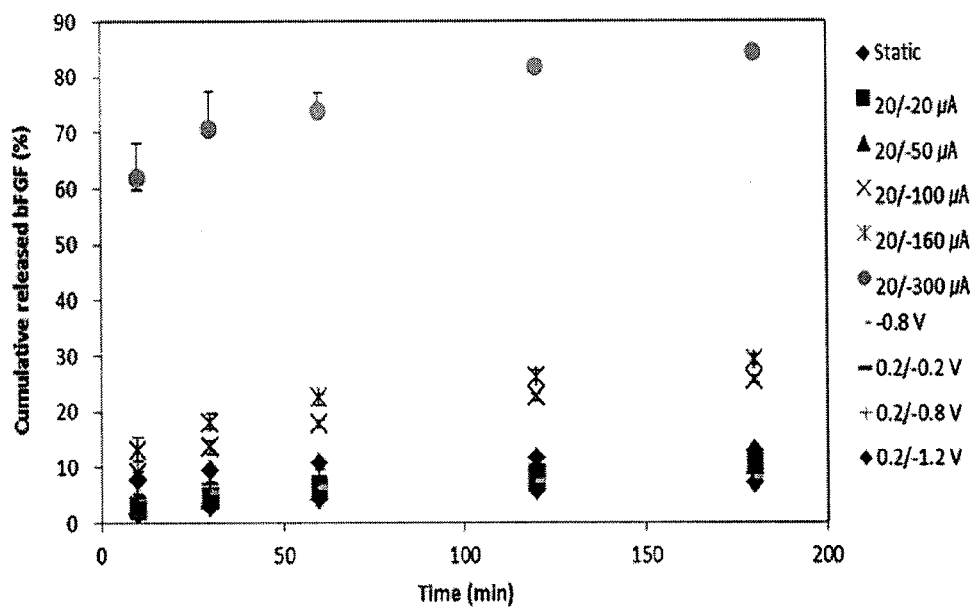
FIG. 7 is a graph showing the time course of cumulative release of bFGF for various electrical stimulations.

FIG. 7 is a graph showing the time course of cumulative release of bFGF for various electrical stimulations. In the all kinds of potential control and in the case of current control with 20/−20 μA and 20/−50 μA, very slow release rates of bFGF were observed after showing small initial burst, and this behavior was very similar to the control case without electrical stimulation. By the application of 20/−100 μA or 20/−160 μA, continuous release of bFGF during electrical stimulation was observed after initial burst of 9% and 13%, respectively. About 25% in the case of electrical stimulation of 20/−100 μA and about 29% in the case of electrical stimulation of 20/−160 μA of total bFGF were released continuously during electrical stimulation. On the contrary, upon applying electrical stimulation of 20/−300 μA, over 60% of loaded bFGF was released as an initial burst, followed by slow release. Therefore, it was possible to modulate the release of loaded bFGF on heparin-immobilized gold surface by applying controlled current.

Figure 8A:
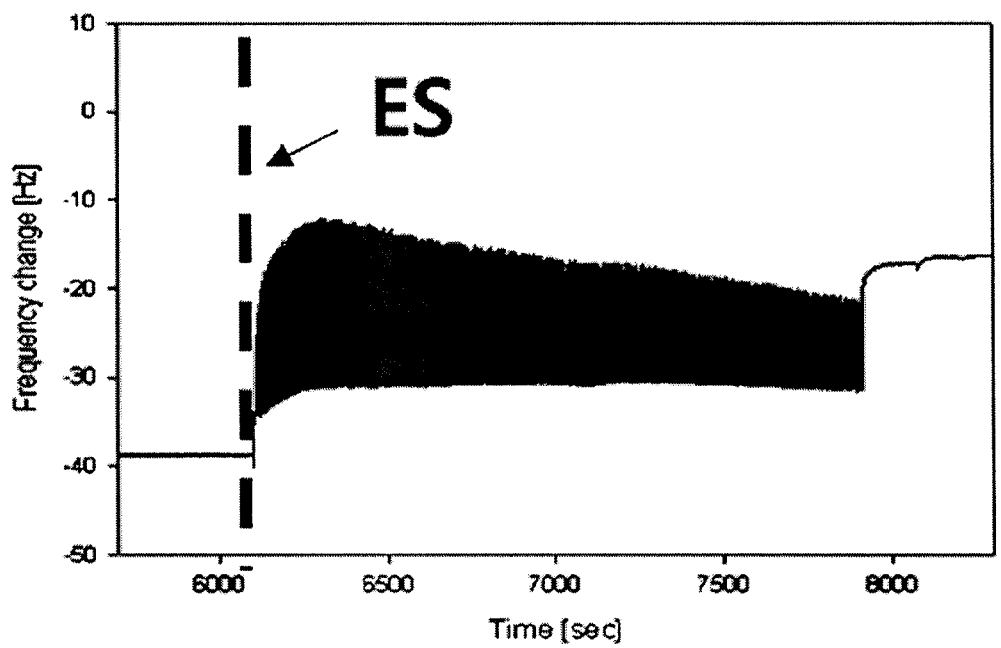
FIGS. 8a to 8c are graphs showing results of monitoring the frequency changes in chemisorbed Hep-SH by various electrical stimulations (8a: 20/−300 μA, 30 min; 8b: 20/−100 μA, 30 min; 8c: 0.2/−0.8 V, 10 min) using QCM-D with electrochemical module (EQCM-D).
Figure 8B:
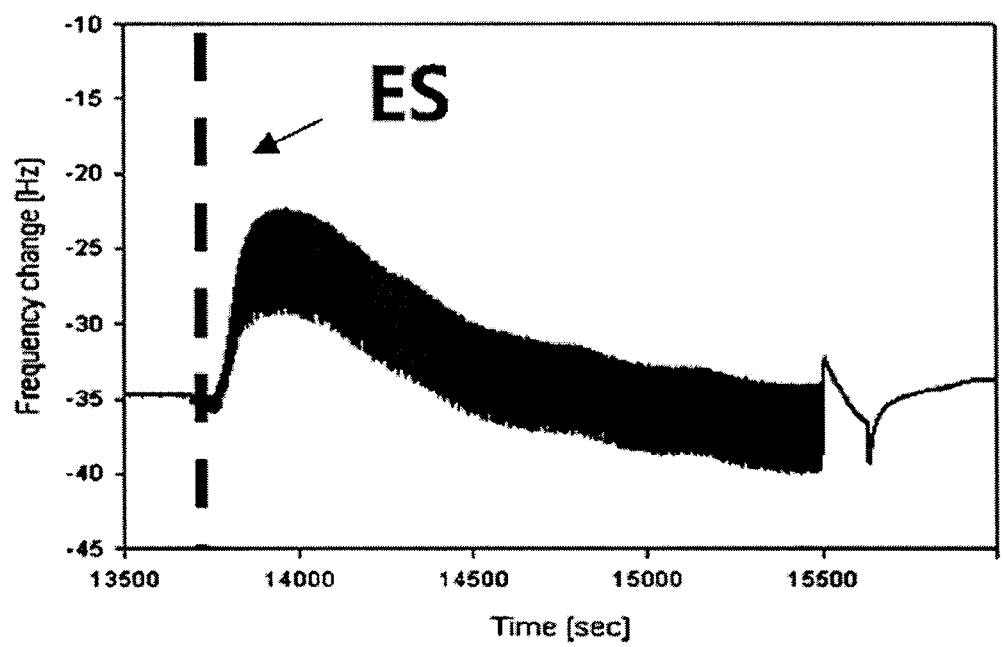
Figure 8C:
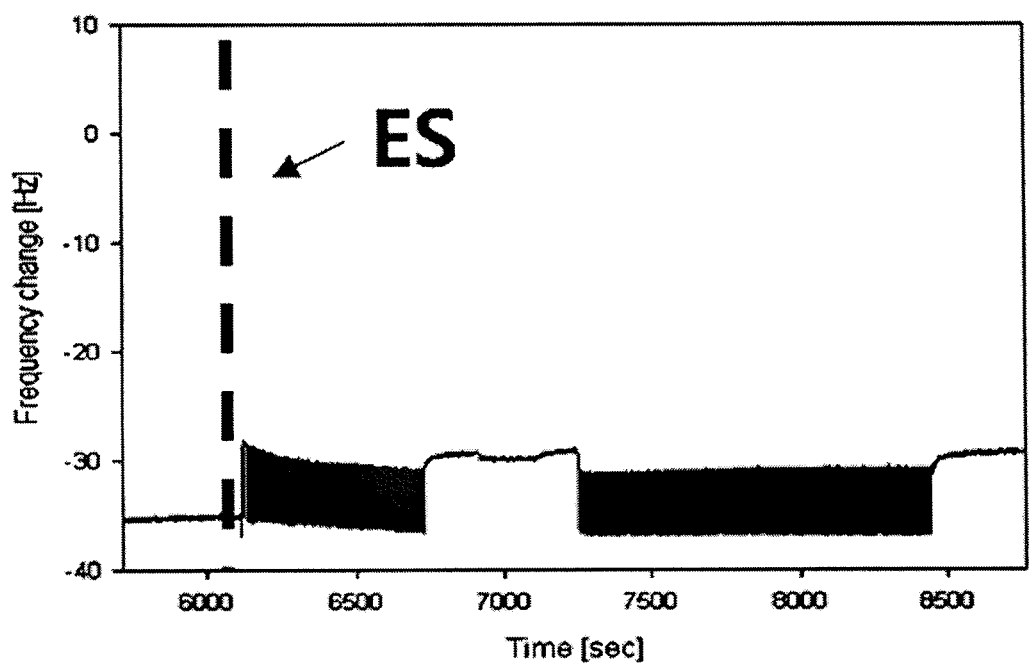

To characterize the release mechanism of bFGF by electrical stimulation, the frequency changes in chemisorbed Hep-SH by various electrical stimulations were monitored by using QCM-D with electrochemical module (EQCM-D). As shown in FIG. 8a to FIG. 8c, an immediate and significant decrease (~60%) in the adsorbed Hep-SH was observed by the application of electrical stimulation of 20/−300 μA, whereas small change (~5%) in the adsorbed mass was observed either by electrical stimulation of 20/−100 μA or 0.2/−0.8 V. This result suggests that the reductive potential applied by electrical stimulation of 20/−100 μA was not large enough to induce the desorption of chemisorbed Hep-SH. Also, this result clearly indicates that the main mechanism of continuous and stimulated release of bFGF by electrical stimulation of 20/−100 μA was not the desorption of Hep-SH. A potential reason might be the effect of ion imgration driven by negative charges accumulated on gold surface, which would induce an environment of a high salt concentration also near the adsorbed heparin, thus provide a driving force for the dissociation of bound growth factor. On the other hand, an immediate and significant decrease in mass by electrical stimulation of 20/−300 μA suggests that the large initial busrt in bFGF release observed upon the application of that current control is mainly responsible from the desorption of Hep-SH from gold surface.

Figure 9A:
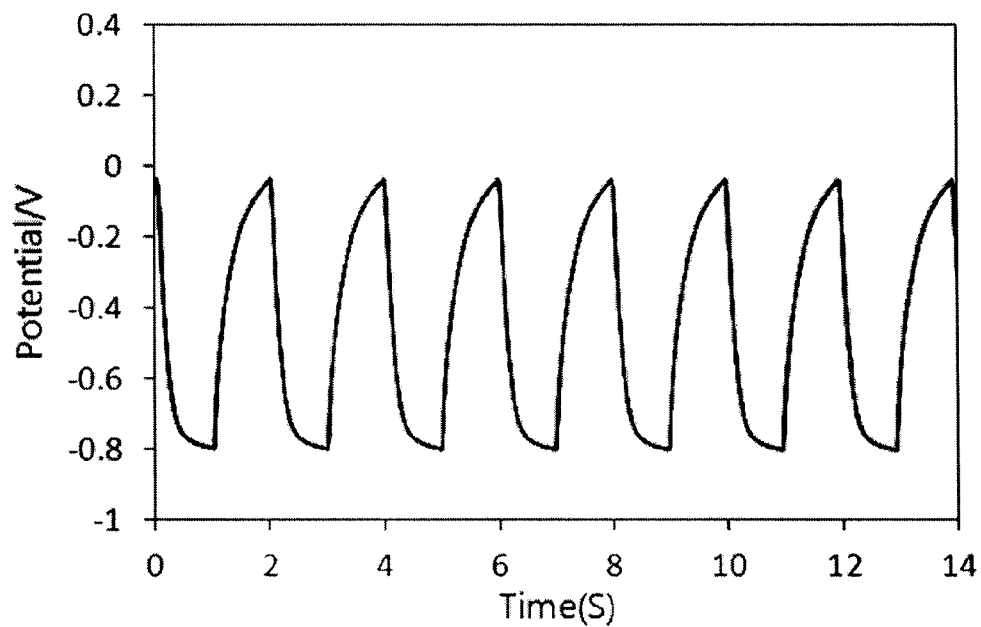
FIGS. 9a to 9f are graphs showing applied potential (FIG. 9a and FIG. 9b), applied current (FIG. 9c and FIG. 9d), and cumulative charge (FIG. 9e and FIG. 9f), where current stimulation (20/−100 μA.
Figure 9B:
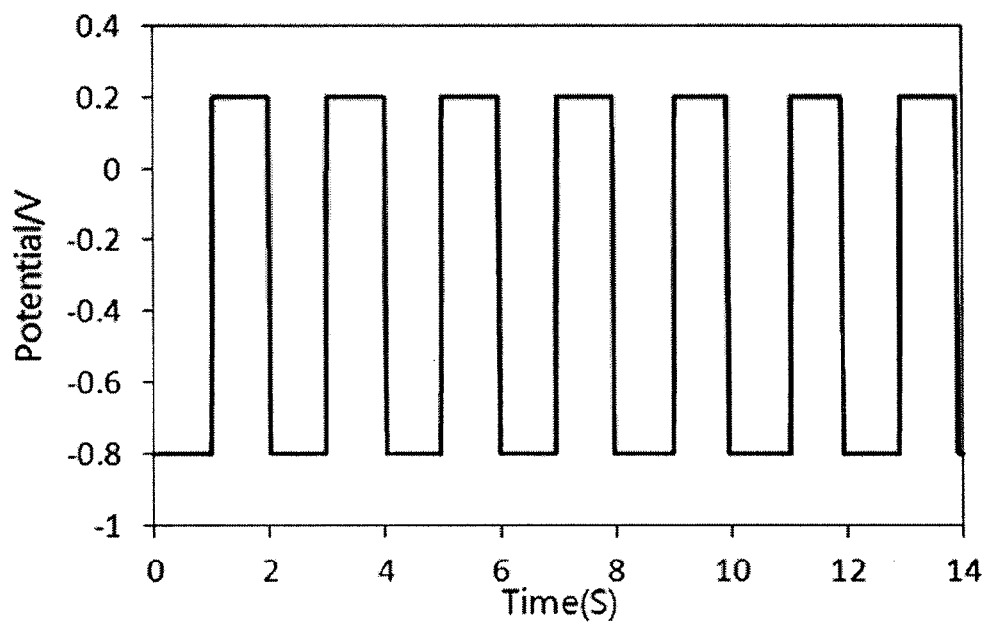
Figure 9C:
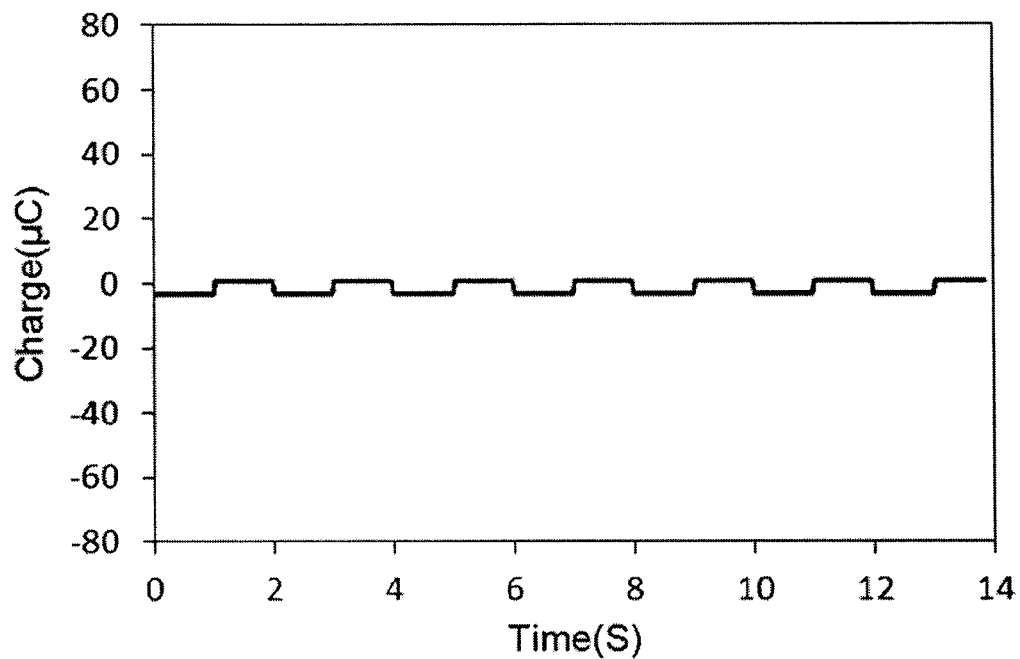
Figure 9D:
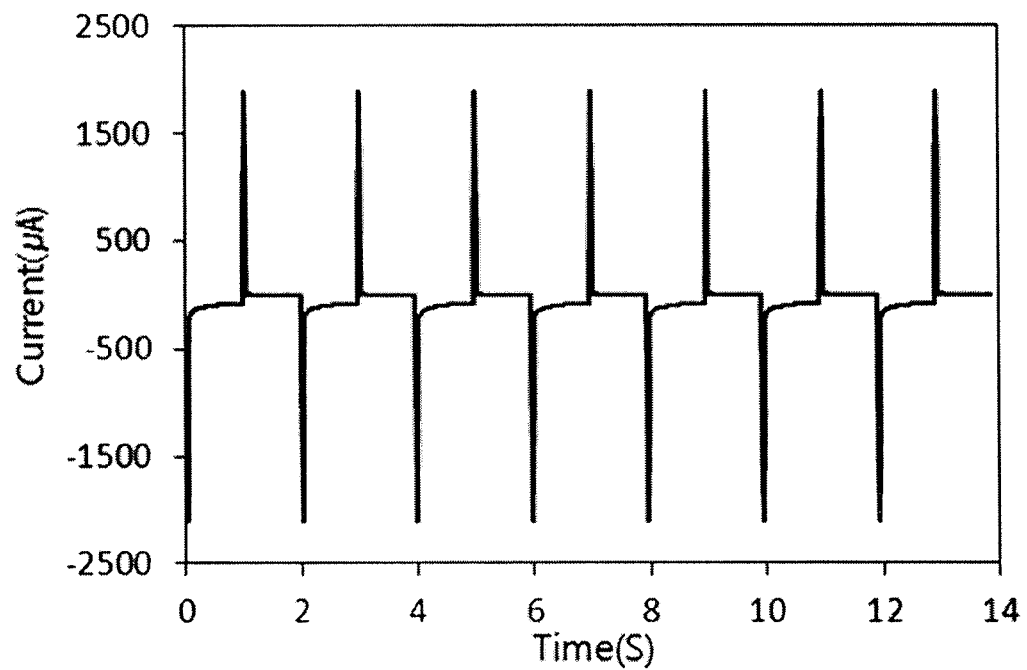
Figure 9E:
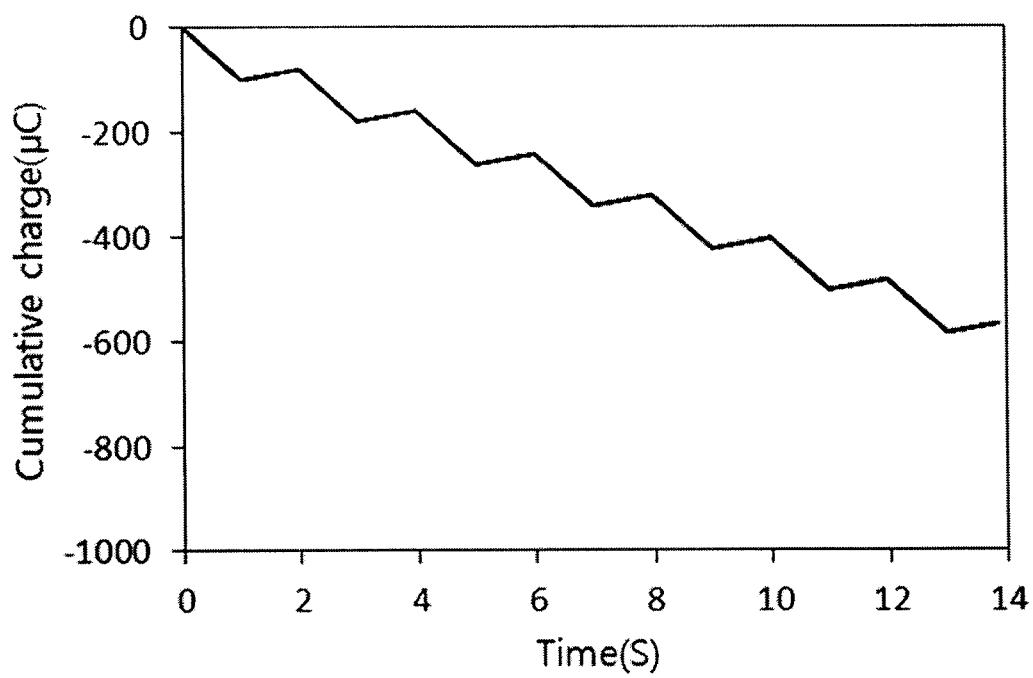
Figure 9F:
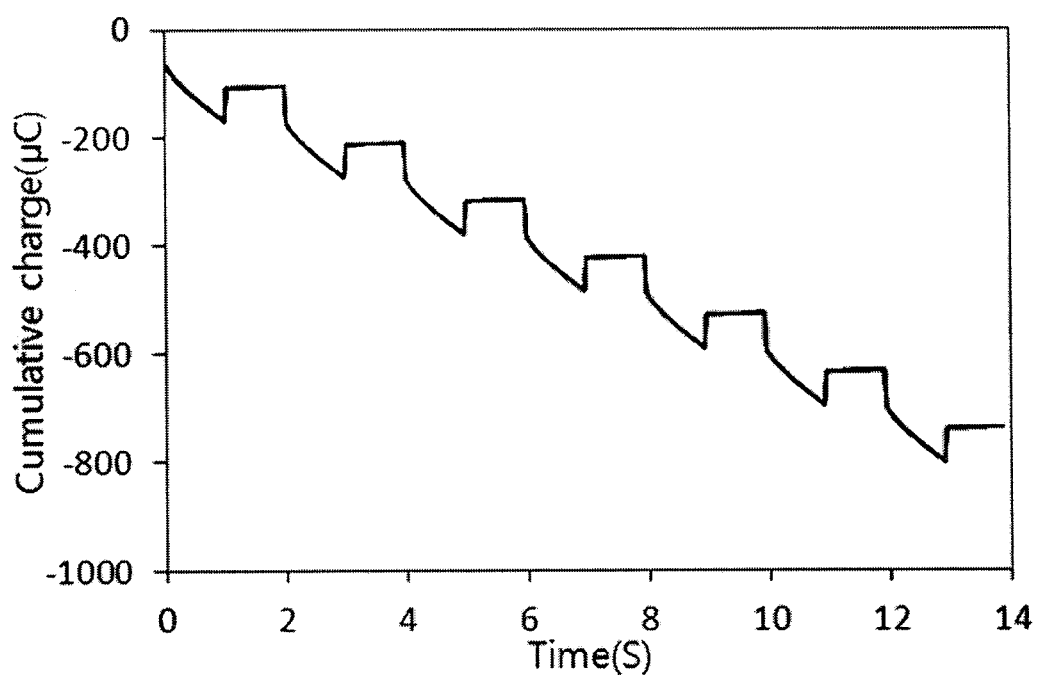

It has been reported previously that a charge delivery by current control has several advantages over potential control (Guixin S, Mahmoud R, Shiyun M, Ze Z. Electrical stimulation enhances viability of human cutaneous fibroblasts on conductive biodegradable substrates, *Journal of Biomedical Materials Research*, 2007, 39, 1027-1037). First, upon applying a potential as potential control, the current of maximum value was generated at the beginning of the pulse and then stimulation efficiency decreased throughout the duration of stimulation by the decrease of current, as shown in current control (FIG. 9d). However, in the case of current control, the current of maximum value was maintained throughout the duration of stimulation. Second, an increase in resistance for electrical stimulation resulted in an additional voltage drop in the case of potential control, which caused the decrease in current and stimulation efficiency. Also, when the direction of applied stimulation was changed, the discharge of potential control was relatively rapid than that of current control (FIG. 9a and FIG. 9b). Therefore, current control had more time to accumulate greater charges at working electrode.

Figure 10:
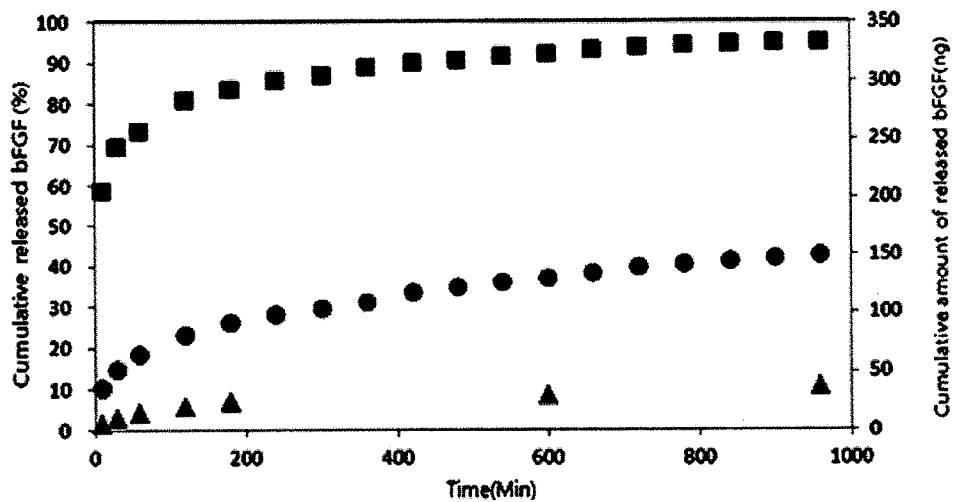
FIG. 10 is a graph showing long-term (16 hrs.) release profile of bFGF by the current stimulations.

Meanwhile, long term (16 hr) release profiles of bFGF upon electrical stimulations are shown in FIG. 10. Upon the current stimulation of 20/−300 μA, the release profile of bFGF is characterised by a large initial burst of ~60% followed by a slow release up to 60 h. After completion of this experiment, the gold electrode was characterized with cyclic voltammetry, and the CV curve was the same with that of bare gold electrode, confirming the complete release of Hep-SH as well as bFGF. Therefore, using the current stimulation of 20/−300 μA, stimulated release of growth factor is possible mediated by the desorption of Hep-SH from gold for a relatively short duration. Upon the current stimulation of 20/−100 μA, the release profile of bFGF is characterised by a small initial burst of ~10% followed by a continuous and sustained release. After 16 h, over 40% of the loaded bFGF was released.

Figure 11:
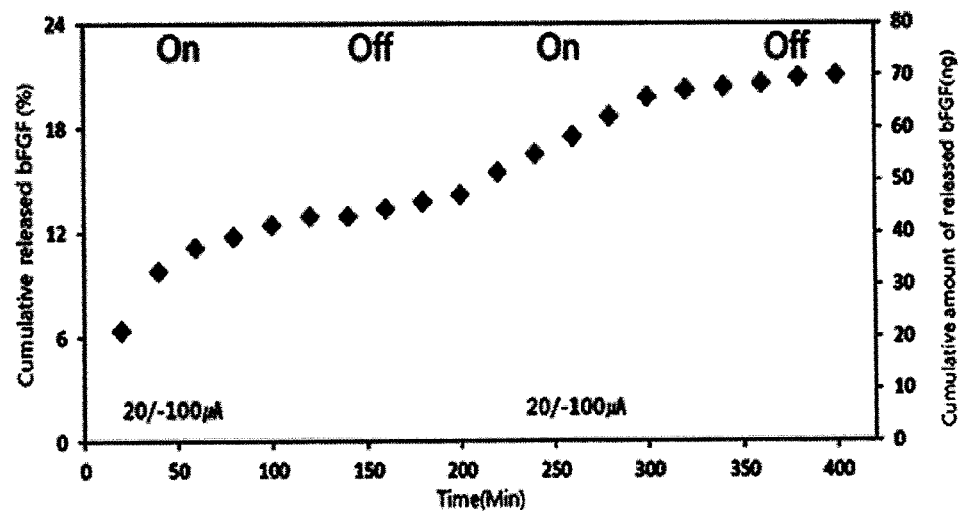
FIG. 11 is a graph showing the time-course of release when the release rate of bFGF was controlled by the turn-on and -off of current stimulation of 20/−100 μA.

By turning-on and turning-off the current stimulation of 20/−100 μA, an abrupt control of release rate was also possible (FIG. 11). The current stimulation of 20/−100 μA was applied in a plurality of times for 200 min with the cessation of electrical stimulation for 100 min between electrical stimulations. The release rate was significantly reduced from the on-state to the off-state, and it was increased again by turning on the electrical stimulation. Thus, the reversible modulation of release rate was achieved by modulating electrical stimulation. The amount of bFGF released during the on-state was nearly sixfolds larger amounts than that during the off-state. Therefore, it is apparent that the release of growth factor from gold electrode modified with Hep-SH can be precisely modulated by controlling applied electrical stimulation.

Evaluation Example 4

Cytotoxicity of Electrical Stimulation on Fibroblast Cell

To investigate any cytotoxic effect of electrical stimulation, Balb/c3T3 fibroblast cells ($2 \times 10^4$ cells/slides) were cultured at glass slides and then electrical stimulation with 20/−100 μA was indirectly applied to the cells in culture media of 6 mL for 1 h under the stimulation system composed of conventional three electrodes.

As a result of staining cells treated with electrical stimulation and cells untreated with electrical stimulation by double staining using acridin orange and propidium iodide and observing with a microscope, the viability of fibroblast cells after electrical stimulation showed no noticeable difference between electrically stimulated cells and normal cells. Most of the cells were alive, and the estimated viability was ~94% and ~98% for electrical stimulated cells and normal cells, respectively. Therefore, the result confirms no cytotoxicity of electrical stimulation used for modulation of release of bFGF. Previous reports also verified that directly applied current was safe up to 250 μA for fibroblast cells on gold (Guixin S, Mahmoud R, Shiyun M, Ze Z. Electrical stimulation enhances viability of human cutaneous fibroblasts on conductive biodegradable substrates, *Journal of Biomedical Materials Research,* 2007, 39, 1027-1037).

Evaluation Example 5

Bioactivity of bFGF Released by Electrical Stimulation

Figure 12:
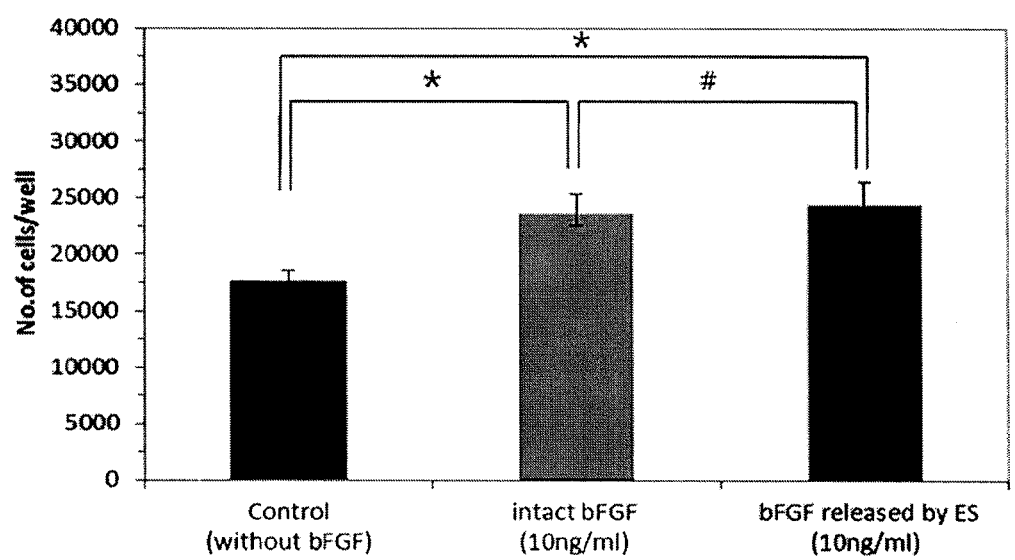
FIG. 12 is a graph showing the number of incubated cells, when Balb/c3T3 cells were treated with bFGF untreated with electrical stimulation or bFGF released by electrical stimulation. For control, Balb/3T3 cells were treated without bFGF.

In the present example, bFGF was used as a growth factor bound on Hep-S.Au. By the application of appropriate control of current profiles, stimulated release of bFGF was observed. In order to estimate the bioactivity of bFGF released by electrical stimulation (20/−100 μA), Balb/c3T3 fibroblast cells were cultured with the addition of pristine bGF or bFGF released by the electrical stimulation at the same concentration (10 ng/mL). Especially, the bFGF was released after 3 day incubation in buffer to check the potential effect of both incubation in buffer and electrical stimulation on the bioactivity of bFGF. The enhanced cell proliferation by the addition of bFGF, estimated by WST-8 assay, was similar in both pristine bFGF and bFGF released by the electrical stimulation (FIG. 12, #p>0.05), showing no decrease in bioactivity was caused during incubation or by electrical stimulation. Therefore, the result proves no deteriorating effect on bioactivity of current application at least in the tested range, which was enough to provide the stimulated, sustained release of growth factor. No decrease in bioactivity during incubation must result from the existence of bFGF as a bound state in heparin-immobilized gold surface via heparin-binding affinity.

As stated above, the present invention provides a method of modulating the release of growth factors easily and effectively, by applying electrical stimulation to heparin immobilized on gold surface. Immobilization of heparin on gold surface was achieved efficiently by using the chemisorptions of thiolated heparin. Spontaneous loading of growth factor onto heparin-immobilized gold was also achieved via heparin-binding affinity of growth factors. Among various electrical stimulations, current control was more effective for increasing the release rate of growth factors, and specifically 20/−100 μA with 1 s pulse was suitable to get continuous and stimulated release of bFGF during the application of electrical stimulation. Long-term release and on/off switchable release were also possible by controlling the electrical stimulation profile. In addition, this current control was safe enough not to cause any cytotoxic effect or damage the bioactivity of released growth factors. Accordingly, the present invention can be applied for various biomedical and biotechnical fields including drug delivery, biosensor, and cell culture, by combining micro-patterning techniques.

According to the present invention, a method of modulating a release rate of various biomolecules having heparin-binding affinity such as growth factors easily and precisely by external electrical stimulations, the method which does not cause cytotoxicity and have any deteriorating effects on cell activity, can be provided.

Although the method of modulating the release of biomolecules having heparin-binding affinity has been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:

1. A method of modulating a release of biomolecules having heparin-binding affinity, comprising:
    preparing thiolated heparin by modifying carboxylic acid group of heparin;
    chemisorbing the thiolated heparin on metal surface by oxidation;
    binding a fibroblast growth factor having heparin-binding affinity to the adsorbed heparin; and
    causing the release of the fibroblast growth factor having heparin-binding affinity by applying electrical stimulation to the complex of metal surface, heparin, and the fibroblast growth factor to achieve controlled release of said fibroblast growth factor.

2. The method of claim 1, wherein the thiolated heparin is prepared by reacting the heparin with cysteamine.

3. The method of claim 1, wherein the metal is biocompatible, and able to react with a thiol group.

4. The method of claim 1, wherein the metal is one or more metals selected from the group consisting of gold, silver, and platinum.

5. The method of claim 1, wherein the electrical stimulation is an application of current from about 100 μA to about −500 μA or application of potential from about 1.5V to about 2.0V.

6. The method of claim 1, wherein the electrical stimulation is an application of current from about 20 μA to about 100 μA.

* * * * *